United States Patent [19]

Bannard et al.

[11] Patent Number: 5,077,316

[45] Date of Patent: Dec. 31, 1991

[54] METAL PHENOXIDE/POLYETHYLENE GLYCOLS CHEMICAL DECONTAMINANT SYSTEM

[75] Inventors: Robert A. B. Bannard, Carp; Alfred A. Casselman, Greely; John G. Purdon; John W. Bovenkamp, both of Kanata, all of Canada

[73] Assignee: Her Majesty Queen as represented by Minister of National Defence Canada, Ottawa, Canada

[21] Appl. No.: 700,921

[22] Filed: Nov. 20, 1984

[30] Foreign Application Priority Data

Nov. 22, 1983 [CA] Canada .................................. 441617

[51] Int. Cl.[5] .......................... A62D 5/00; A61K 7/40

[52] U.S. Cl. .................................... 514/731; 514/723; 514/969

[58] Field of Search ........................ 514/731, 723, 969

[56] References Cited

U.S. PATENT DOCUMENTS

| | | | |
|---|---|---|---|
| 2,391,798 | 12/1945 | Read | 514/731 |
| 3,011,940 | 12/1961 | Bollenback | 514/731 |

OTHER PUBLICATIONS

*The Condensed Chemical Dictionary*, sixth edition, pub. 1961, Reinhold Pub. Co., New York, p. 1049.

*Primary Examiner*—Robert L. Stoll
*Assistant Examiner*—Gary L. Geist
*Attorney, Agent, or Firm*—Nixon & Vanderhye

[57] ABSTRACT

A barrier cream consisting essentially of at least one active ingredient chosen from the alkali metal salts of phenols, dispersed in a substantially anhydrous state in a base medium comprising a polyethylene glycol which has been at least partially etherified to reduce the free hydroxyl group content thereof. These creams are simple to prepare, effective for a reasonable period of time and do not produce adverse skin reaction, and are simple both to apply and to remove. They afford protection against chemical warfare agents of both the V and G types, and against mustard gas (H or HD).

16 Claims, No Drawings

METAL PHENOXIDE/POLYETHYLENE GLYCOLS CHEMICAL DECONTAMINANT SYSTEM

This invention relates to a barrier cream formulation which can be used to protect exposed areas of the body from the effects of chemical warfare agents.

These types of chemical warfare agents which are considered to constitute a major threat are those commonly designated as HD, V and G. The first of these, HD, is an acronym for mustard gas, the 'D' implying that it is distilled. The formula for this compound is $ClCH_2CH_2—S—CH_2CH_2Cl$. It belongs to the vesicant class of chemical warfare agents. V and G stand for the V- and G-series of nerve agents. The G-series tend to be volatile and highly toxic by inhalation, whilst the V-agents are relatively non-volatile, persistent, and highly toxic by the percutaneous route.

Typical examples of these series are GD and VX which have the following formulae:

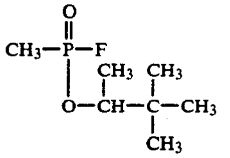

VX (1,2,2-trimethyl)propyl methylphosphono-fluoridate

GD

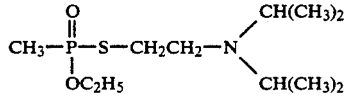

O-ethyl S-2-diisopropylamino-ethyl methylphosphonothiolate

To be of practical use under field conditions, any barrier cream which is to be used as a protection against chemical warfare agents has to exhibit three main properties. First, it must be effective against all three of these types of chemical warfare agents. Second, it must be compatible with human skin and not cause any adverse reactions, at least over a limited period of time. Third, it must provide protection to the wearer for a reasonable period of time. These three criteria effectively exclude many of the currently known decontamination systems which have been devised as a means of destroying chemical warfare agents. The chief difficulty is that such decontamination systems contain reagents which cannot be tolerated on human skin for other than quite brief periods of time. Some of these systems are very alkaline, and some use concentrated active chlorine or bleach solutions. Thus, although these systems are, more or less, efficacious as decontaminants for equipment which has been exposed to chemical warfare agents, they are of no use in protecting people, and give no guide at all as to the sort of reagents that may be used for that purpose.

We have now found a surprisingly simple and efficacious solution to this problem which permits the formulation of a barrier cream which is effective against all three types of agents, causes no adverse skin reactions during the periods of time for which such a barrier cream is likely to be worn, and also provides the wearer with protection for a reasonable period of time.

A particular feature of the creams of this invention is that although they contain a reagent that is potentially extremely basic, for example, potassium phenoxide, they do appear to be compatible with skin.

Thus, in its broadest aspect, this invention provides a barrier cream consisting essentially of at least one active ingredient chosen from the alkali metal salts of mono- and dihydroxy phenols, and alkyl and mono alkoxy substituted phenols, in which the alkyl groups each contain from 1 to 4 carbon atoms, dispersed in a substantially anhydrous state in a base medium comprising a polyethylene glycol which has been partially etherified to reduce the free hydroxyl group content.

Preferably the alkali metal is chosen from sodium and potassium. More preferably the potassium salts are used.

Preferably the salt is of phenol, and thus the most preferred active ingredient is substantially anhydrous potassium phenoxide.

The base medium used in these creams can be chosen from a wide range of compounds, and indeed need not be a single compound at all. The chief requirement is that it provide an adequate cream consistency. The polyethylene glycols being considered here have the general formula $R^1O(CH_2CH_2O)_nCH_2CH_2OR^2$, in which both $R^1$ and $R^2$ are hydrogen. For the creams of this invention, these hydroxyl groups need to be etherified, at least in part, otherwise unwanted side-reactions with the active ingredient will occur. Thus generally at least one, and often both of $R^1$ and $R^2$ will not be hydrogen. Suitable etherifying groups are alkyl groups of up to 4 carbon atoms. Typically the etherifying groups will be methyl or ethyl groups.

The value of n in the above formula can be chosen from a wide range. If n is high enough, for example, to give a molecular weight above 750 or so, then the polyethylene glycol ether will itself provide the required consistency for the cream. Alternatively, if n is small, for example, the compound $CH_3O(CH_2CH_2O)_3CH_2CH_2OCH_3$ known as "tetraglyme", then the polyethyleneglycol ether is a liquid and cannot provide a cream by itself. It may be thickened by adding to it any of the substances commonly used in pharmaceutical creams for this purpose, such as silicas, titania, Fuller's earth, clays, bentonite, and so forth. The filler used also has to be one which will not react with the active ingredient. Thus an "active" silica may need to be etherified before use.

The barrier creams of this invention also proffer a further unexpected advantage. It was noted above that the equipment decontamination systems commonly used cannot be used on skin due to their chemical nature. This also means that such systems tend to be of questionable use for decontaminating porous equipment surfaces such as fabrics and webbing. If these chemical solutions are left in contact with such porous materials long enough to penetrate them adequately, then they are also likely to damage the materials as well. This appears not to be the case with the creams of this invention, which can be left in contact with porous contaminated surfaces for extended periods of time without any damage resulting. For this application of the creams of this invention, a stable foam formulation of the type commonly used in shaving creams and the like is also advantageous.

It is noted above that the barrier creams of this invention do not affect the skin. It is believed that this is, at least in part, due to the fact that the salts used are free of base: for example, the potassium phenoxide used is free, substantially, of potassium hydroxide. We have devised a technique whereby these active ingredients can be made in a substantially pure state, containing only insignificant amounts, if any, of the free alkali or alkaline earth metal hydroxide.

The invention will now be described by way of reference to the following Examples.

EXAMPLE 1

Preparation of Potassium Phenoxide

Phenol, 25 g, sublimed under vacuum, was dissolved in 150 ml dry ether and added by a dropping funnel to a stirred suspension of 9.21 g of powdered potassium in a dry mixture of toluene, 150 ml and dry ether, 150 ml. After 24 hours reflux, the mixture was filtered and a colorless solid obtained which was washed twice with dry ether. The salt was dried under high vacuum at 56° for 24 hours. M.p.: 285°-289° C. Analysis: K, theory: 29.57; found 29.08. Purification by dissolution in hot acetone, and precipitation with dry ether raised the K analysis figure to 29.17.

In a similar fashion, the alkali metal salts of other phenols may be prepared, including both the alkyl derivatives of phenol such as cresols, and the alkyl and mono-alkoxy derivatives of catechol and resorcinol, such as 2-methoxy phenol and the like. The alkyl groups in these phenol derivatives may contain from 1 to 4 carbon atoms.

EXAMPLE 2

Penetration of Mustard Gas Through Barrier Creams

The apparatus consists of a series of separate cells of circular cross-section over which are fixed approximately 2¼ inch-diameter samples of 0.022 mm-thick polyethylene film cemented to rubber annuli, with an internal diameter of 2 inches. The annuli are 1 mm or 0.5 mm in depth. The cavities of these annuli are filled to the top with the cream to be tested, using a liquid filling technique following liquefaction of the creams by heating to 40°-50° C. After the solution has cooled and the cream has set, the samples are carefully examined for discontinuities, i.e. broken seals at the edge of the annuli or bubbles and if none are found the samples are placed in the test apparatus, $5 \times 1$ μL drops of mustard gas are applied by hypodermic needle touch-off to the surface of the cream in the usual manner and the amount of agent which penetrates the cream and the polyethylene film in 24 h is determined. The determination is made by sweeping air from the cavity below the polyethylene film and absorbing the mustard gas in a trapping solvent. This solution is then analyzed by a standard gas chromatographic method to determine the amount of mustard gas which has penetrated both the cream and the polyethylene film.

The following results were obtained. The cream used was 0.625M potassium phenoxide in polyethylene glycol 750 monomethyl ether (i.e. the monomethyl ether of a polyethylene glycol having an average molecular weight of 750). In each case, more than one sample was run. The control was provided by placing $5 \times 1$ μl drops of mustard on annulus-polyethylene assemblies containing no barrier cream.

-continued

| Film Thickness, mm. | Average Control | Mustard Gas Penetration, μg Barrier Cream |
|---|---|---|
| 1.0 | 457 | 0 |
| 1.0 | 386 | 8.9 |
| 0.5 | 386 | 15.9 |

EXAMPLE 3

Skin Tests of Barrier Creams on Guinea Pigs

For these tests, the barrier cream used comprised an 0.625M or an 1.25M solution of potassium phenoxide in dry tetraglyme [this compound has the formula $CH_3O(CH_2CH_2O)_3CH_2CH_2OCH_3$] to which finely divided silica (Cab-O-Sil, trademark) was added. A blank cream, comprising tetraglyme and silica alone in the same ratios was also used as a composition standard. In some tests the cream contained 700 mg silica per 10 ml tetraglyme or solution, whilst in others 630 mg was used. In both cases, the aim was to obtain a smooth, lump-free cream that spreads easily. There is no reason to believe that the precise amount of silica has any bearing on the results obtained. In each of the tests, a small area, up to about 25 $cm^2$, on the backs of the test animals was depilated by clipping followed by application of a proprietary hair remover. After depilation the animals were caged individually to avoid damage to the depilated area.

A. Tests with GD, 1,2,2-trimethylpropyl methylphosphonofluoridate

Dose Regime

Animals No. 1 and 2: The barrier cream was spread as evenly as possible on the depilated back to obtain a layer of 1 to 1.5 mm thickness on an area of 25 $cm^2$. A 10-μl volume (equivalent to 10 mg) of neat GD was applied on the cream as a streak less than 1 cm long (No. 1) or as a discreet spot (No. 2). The animals were restrained to avoid oral ingestion or contamination of the equipment, as well to prevent transfer and accidental contact of the experimental animals with the applied GD.

Animals No. 3 and 4: A 10-μl volume (equivalent to 10 mg) each was applied as a discreet spot on the depilated skin without any cream treatment.

Animal No. 5: Approximately 2- to 2.5-mm thick barrier cream was applied on an area of 25 $cm^2$ on the depilated back. Five 10-μl volumes of neat GD were applied as discreet and separate spots on the barrier cream. The total amount applied was equivalent to 50 mg of GD.

Animal No. 6: The blank barrier cream was spread over the 25-$cm^2$ depilated back to obtain a 1- to 1.5-mm thick layer. A 10-μl volume (~10 mg) of neat GD was applied over the cream.

Animal No. 7: The barrier cream was spread evenly over a 25-$cm^2$ area to obtain a layer of cream less than 1 mm thick. Four 10-μl volumes (40 mg) of neat GD were applied as discreet spots on the cream spread on the depilated back of a 585-g guinea pig. This dose was equivalent to 68 mg/kg body weight.

Animal No. 8: The blank cream was spread over a 25-$cm^2$ area to obtain a layer of cream less than 1 mm thick. Five 10-μl volumes (50 mg) of neat GD were applied as discreet spots on the cream spread on the skin of a 730-g guinea pig. This dose is equivalent to 69 mg/kg body weight.

The experiments were conducted in a fume hood with an average air-flow of 250 fpm. The animals were observed for overt signs of toxicity and mortality for 14 days. The cream was left on the skin for either 24 or 48 h before rinsing it off with lukewarm water. The animals were observed further for skin irritation. On Day 12 or 13, the animals were again depilated with the same proprietary depilatory cream for better observation of any skin lesion.

Results

Table 1 shows the test results. All animals that were treated with barrier cream and challenged with lethal doses of GD survived and appeared normal.

TABLE 1

Detailed Experimental Results

| Animal No. | Protection | Amount of GD Used (mg) | Observations |
|---|---|---|---|
| 1 | Barrier Cream | 10 | No overt signs of toxicity; surviving 48 h post dose administration; slight skin erythema observed only after 48 h continuous exposure to the barrier cream. |
| 2 | Barrier Cream | 20 | No overt signs of toxicity; surviving 48 h later; slight skin erythema observed only after 48 h continuous exposure to the barrier cream; all but about 5 mm in diameter of slightly erythematous spot remains 5 days later;* complete remission of the skin lesion on the 6th day. |

*The cream was rinsed off the skin 48 h post application; animals not observed on the weekend.

| Animal No. | Protection | Amount of GD Used (mg) | Observations |
|---|---|---|---|
| 3 | None (No Cream) | 10 | Skin fasiculation began within 9 min, anxious, progressive tremor, convulsion, paralysis of legs, rapid respiration, lacrimation; dired in 14 min post dose administration |
| 4 | None (No Cream) | 10 | Skin fasiculation began within 7 min, progressive tremors, anxious, rapid respiration, salivation, lacrimation, eyes dilated and turned opaque at the centre, leg paralysis, convulsion, died in about 5 h post dose administration. |
| 5 | Barrier Cream | 50 | No overt signs of toxicity; surviving 48 h post dose administration; very slight skin erythema even after 48 h of continuous exposure to the barrier cream; erythema disappeared 5 days later. |
| 6 | Blank Cream | 10 | Skin fasiculation a few minutes later, rapid respiration, less responsive to touch, no severe tremor observed, appeared recovered in about 2 h post dose administration; surviving 48 h post dose administration; no skin erythema even after 48 h of continuous contact with the blank cream.* |
| 7 | Barrier Cream | 40 (68 mg/kg) | No overt signs of toxicity; appears normal surviving 24 h; no skin irritation.* |
| 8 | Blank Cream | 50 (68 mg/kg) | Skin fasiculation 21 min post dose administration; progressed to tremors, rapid respiration, convulsion; less responsive to touch; found dead approximately 1.5 h post dose administration. |

*The cream was rinsed off the skin 24 h post administration

B. Tests with VX, O-ethyl 5-2-diisopropylaminoethyl methylphosphonothiolate

Using a similar procedure, the following results were obtained.

Results from the test of a potassium phenoxide/tetraglyme barrier cream for protection of guinea pigs against VX.

| Test No.[a] | No. animals used | Dose Volume (neat VX) | Actual Dose (μg/kg) | Mortality: Survival | Survival (%) |
|---|---|---|---|---|---|
| A | Group a.3 | 0 | 0 | 0:3 | 100 |
| | Group b.2 | 1 μl | 2152 and 2700 | 2:0 | 0 |
| B. | 2 | 1 μl | 2246 and 2549 | 2:0 | 0 |
| C. | Group a.7 | 1 μl | 1354 to 2457 | 2:5 | 71 |
| | Group b.8 | 2 × 1 μl | 4068 to 5089 | 7:1 | 12 |
| D. | Group a.8 | 2 × 1 μl | 3617 to 4530 | 1:7 | 88[b] |

-continued

| Results from the test of a potassium phenoxide/tetraglyme barrier cream for protection of guinea pigs against VX. | | | | | |
|---|---|---|---|---|---|
| Test No.[a] | No. animals used | Dose Volume (neat VX) | Actual Dose (μg/kg) | Mortality: Survival | Survival (%) |
| | Group b.1 | 3 × 1 μl | 6125 | 0:1 | 100 |

[a]A = Without cream (control).
B = 0.67 mm blank cream (without potassium phenoxide).
C = 0.67 mm barrier cream containing 0.625M potassium phenoxide.
D = 0.67 mm barrier cream containing 1.25M potassium phenoxide.
[b]The animal that died looked well and was feeding until 5 h post dose administration, when pronounced muscle spasm was noticed; later it was dead at 5.6 h. Survivors did not show overt intoxication, were feeding well after dose administration, and gained body weight until sacrificed.

C. Tests with HD, distilled mustard gas or 2,2'-dichlorodiethylsulphide

Using a similar procedure, the following results were obtained. The assessment of the skin reaction followed essentially the method of Draize et al. In each case, the total possible score for erythema, eschar and edema is 4, ranging from zero for no observed effect, to 4 for perceptible injuries of some magnitude. The total possible 'Skin Reaction Score' is thus 12.

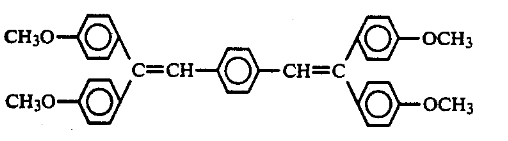
[1]

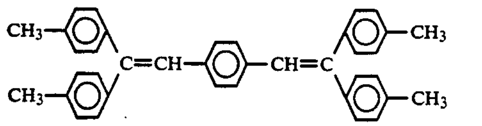
[2]

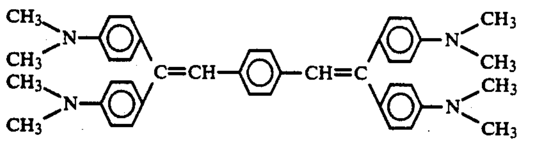
[3]

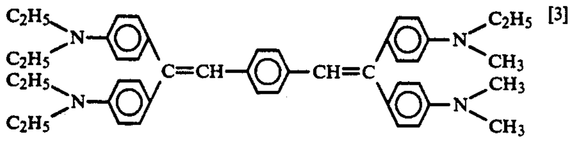
[3]

The embodiments of the invention in which an exclusive property or privilege is claimed are defined as follows:

1. A barrier cream consisting essentially of at least one active ingredient selected from the alkali metal salts of mono and dihydroxy phenols, and alkyl and mono alkoxy substituted mono and dihydroxy phenols, in which the alkyl and alkoxy groups each contain from 1 to 4 carbon atoms, dispersed in a substantially anhydrous state in a base medium comprising a polyethylene glycol which has been at least partially etherified with at least one alkyl group of up to 4 carbon atoms to reduce the free hydroxyl group content of the polyethylene glycol.

2. A barrier cream according to claim 1 wherein the alkali metal is selected from sodium and potassium.

3. A barrier cream according to claim 2 wherein the alkali metal is potassium.

4. A barrier cream according to claim 3 wherein the active ingredient is potassium phenate.

5. A barrier cream according to claim 1 wherein the polyethylene glycol base has the general formula $R^1O(CH_2CH_2O)_nCH_2CH_2OR^2$ in which $R^1$ and $R^2$ each independently represent hydrogen or an alkyl group and n is an integer of at least one.

6. A barrier cream according to claim 5 in which $R^1$ is hydrogen, and $R^2$ is an alkyl group of up to 4 carbon atoms.

7. A barrier cream according to claim 6 in which $R^2$ is a methyl or ethyl group.

8. A barrier cream according to claim 5 in which both $R^1$ and $R^2$ are alkyl groups of up to 4 carbon atoms.

9. A barrier cream according to claim 8 in which both $R^1$ and $R^2$ are methyl or ethyl groups.

10. A barrier cream according to claim 9 in which both $R^1$ and $R^2$ are methyl groups.

11. A barrier cream according to claim 5 in which $R^1$ and $R^2$ are methyl, and n is three.

12. A barrier cream according to claim 5 in which $R^1$ is hydrogen, $R^2$ is methyl, and n has a value sufficient to provide an average molecular weight of at least 750.

13. A barrier cream according to claim 5 further including an inert powder thickener.

14. A barrier cream according to claim 11 further including an inert powder thickener.

15. A barrier cream according to claim 13 wherein the inert thickener is fine particle size silica.

16. A barrier cream according to claim 1 wherein the base medium comprises a mixture of two different polyethylene glycols.

* * * * *

UNITED STATES PATENT AND TRADEMARK OFFICE
CERTIFICATE OF CORRECTION

PATENT NO. : 5,077,316

DATED : December 31, 1991

INVENTOR(S) : BANNARD et al

It is certified that error appears in the above-identified patent and that said Letters Patent is hereby corrected as shown below:

Column 7, lines 25-47 (all formulas) should be deleted.

Column 7, after line 23, insert the tables as shown on the attached sheet.

Signed and Sealed this

Twenty-second Day of June, 1993

Attest:

MICHAEL K. KIRK

*Attesting Officer* *Acting Commissioner of Patents and Trademarks*

Results from the test of a potassium phenoxide/tetraglyme barrier cream for protection of guinea pigs against HD poisoning.

| Test Number and Animal No. | Spot Designation | Skin Reaction Score: Erythema | Skin Reaction Score: Eschar | Skin Reaction Score: Edema | Mean Total Skin Reaction Score |
|---|---|---|---|---|---|
| I. Control | | | | | |
| 55 | A | 4 | 4 | 2 | |
| 56 | A | 0 | 4 | 2 | |
| | B | 1 | 4 | 2 | |
| 68 | A,B | 4 | 4 | 4 | |
| Total score/total spots | | 13/5 | 20/5 | 14/5 | |
| Average score/spot | | 2.6 | 4.0 | 2.8 | 9.4 |
| II. Blank Cream | | | | | |
| 68 | A,C,D | 4 | 0 | 0 | |
| | B | 4 | 4 | 0 | |
| 69 | A | 3 | 4 | 0 | |
| | B,C | 3 | 4 | 0 | |
| | D | 3 | 0 | 0 | |
| 70 | A | 3 | 4 | 0 | |
| | B | 3 | 0 | 0 | |
| | C | 4 | 4 | 0 | |
| | D | 3 | 0 | 0 | |
| Total score/total spots | | 41/12 | 24/12 | 0/12 | |
| Average score/spot | | 3.4 | 2.0 | 0.0 | 5.4 |